United States Patent
Satake et al.

(10) Patent No.: US 11,125,990 B2
(45) Date of Patent: Sep. 21, 2021

(54) ENDOSCOPE DISTAL END PORTION, ENDOSCOPE, AND METHOD OF MANUFACTURING ENDOSCOPE DISTAL END PORTION

(71) Applicant: OLYMPUS CORPORATION, Tokyo (JP)

(72) Inventors: Nau Satake, Yokohama (JP); Mikio Nakamura, Tokyo (JP); Takanori Sekido, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/850,083

(22) Filed: Apr. 16, 2020

(65) Prior Publication Data

US 2020/0241280 A1 Jul. 30, 2020

Related U.S. Application Data

(63) Continuation of application No. PCT/JP2017/038083, filed on Oct. 20, 2017.

(51) Int. Cl.
*G02B 23/26* (2006.01)
*H04N 5/225* (2006.01)
*G02B 23/24* (2006.01)

(52) U.S. Cl.
CPC ........... *G02B 23/243* (2013.01); *G02B 23/26* (2013.01); *H04N 5/2253* (2013.01); *H04N 5/2254* (2013.01); *H04N 2005/2255* (2013.01)

(58) Field of Classification Search
None
See application file for complete search history.

(56) References Cited

U.S. PATENT DOCUMENTS 4,895,138 A * 1/1990 Yabe .................. A61B 1/05
  348/E5.027
5,050,584 A * 9/1991 Matsuura ........... A61B 1/00068
  600/130

(Continued)

FOREIGN PATENT DOCUMENTS

JP H07-134256 A 5/1995
JP H08-052108 A 2/1996

(Continued)

OTHER PUBLICATIONS

International Search Report dated Dec. 26, 2017 issued in PCT/JP2017/038083.

*Primary Examiner* — Irfan Habib
(74) *Attorney, Agent, or Firm* — Scully, Scott, Murphy & Presser, P.C.

(57) ABSTRACT

An endoscope distal end portion includes: a channel that is tubular, the channel being where a surgical tool is to be inserted in; a light guide configured to guide illumination light emitted from a light source; an imager configured to capture an image of an observed region illuminated with the illumination light from the light guide; and a fixing member that is made of resin and that has a columnar outer shape, the fixing member being configured to seal around the channel, the light guide, and the imager, wherein the channel is in contact with the imager, and the light guide is in contact with at least one of the channel and the imager, and a contact surface of the channel in contact with the light guide or a contact surface of the imager in contact with the light guide has a groove or a projection formed thereon.

6 Claims, 7 Drawing Sheets

(56) References Cited

U.S. PATENT DOCUMENTS

| | | | | |
|---|---|---|---|---|
| 5,291,375 | A * | 3/1994 | Mukai | H05K 3/3421 |
| | | | | 361/760 |
| 5,430,475 | A * | 7/1995 | Goto | A61B 1/05 |
| | | | | 348/65 |
| 5,868,664 | A * | 2/1999 | Speier | A61B 1/042 |
| | | | | 600/112 |
| 6,040,612 | A * | 3/2000 | Minami | H01L 27/14618 |
| | | | | 257/432 |
| 6,095,970 | A * | 8/2000 | Hidaka | A61B 1/00124 |
| | | | | 600/109 |
| 6,945,929 | B2 * | 9/2005 | Ando | A61B 1/00114 |
| | | | | 348/45 |
| 7,091,599 | B2 * | 8/2006 | Fujimori | H01L 31/02002 |
| | | | | 257/692 |
| 7,166,537 | B2 * | 1/2007 | Jacobsen | A61B 1/05 |
| | | | | 438/240 |
| 8,118,732 | B2 * | 2/2012 | Banik | A61B 1/018 |
| | | | | 600/117 |
| 8,471,392 | B2 * | 6/2013 | Kojima | A61B 1/05 |
| | | | | 257/783 |
| 8,520,100 | B2 * | 8/2013 | Reshef | H04N 5/3765 |
| | | | | 348/241 |
| 8,654,184 | B2 * | 2/2014 | Murayama | G02B 23/2484 |
| | | | | 348/65 |
| 8,666,135 | B2 * | 3/2014 | Tomoto | G06T 7/0012 |
| | | | | 382/128 |
| 8,876,702 | B2 * | 11/2014 | Takahashi | A61B 1/0008 |
| | | | | 600/134 |
| 8,944,998 | B2 * | 2/2015 | Yamamoto | A61B 1/051 |
| | | | | 600/110 |
| 9,144,664 | B2 * | 9/2015 | Jacobsen | A61B 1/05 |
| 2007/0270638 | A1 * | 11/2007 | Kitano | A61B 1/00098 |
| | | | | 600/104 |
| 2012/0220826 | A1 * | 8/2012 | Yamamoto | A61B 1/051 |
| | | | | 600/109 |
| 2012/0310043 | A1 * | 12/2012 | Hu | A61B 1/0011 |
| | | | | 600/109 |

FOREIGN PATENT DOCUMENTS

| | | |
|---|---|---|
| JP | 2000-023904 A | 1/2000 |
| JP | 2008-253451 A | 10/2008 |
| JP | 2016-147090 A | 8/2016 |
| JP | 2016-150103 A | 8/2016 |
| JP | 2017-023210 A | 2/2017 |

* cited by examiner

ENDOSCOPE DISTAL END PORTION, ENDOSCOPE, AND METHOD OF
MANUFACTURING ENDOSCOPE DISTAL
END PORTION

CROSS-REFERENCE TO RELATED
APPLICATION

This application is a continuation of International Application No. PCT/JP2017/038083, filed on Oct. 20, 2017, the entire contents of which are incorporated herein by reference.

BACKGROUND

1. Technical Field

The present disclosure relates to endoscope distal end portions, endoscopes, and methods of manufacturing endoscope distal end portions.

2. Related Art

In the related art, endoscopes acquire in-vivo images inside subjects, such as patients, through insertion of flexible insertion units into the subjects, the flexible insertion units having imagers provided at distal ends thereof and being elongated. Proposed for the purpose of reduction in diameter of a distal end portion of such an endoscope is an endoscope including: a first unit having a surgical tool channel in a distal end tube formed approximately cylindrically, the surgical tool channel having an approximately semi-cylindrically shaped cross section; and a second unit having a subject image observation means (as seen in Japanese Laid-open Patent Publication No. 08-52108).

SUMMARY

In some embodiments, an endoscope distal end portion includes: a channel that is tubular, the channel being where a surgical tool is to be inserted in; a light guide configured to guide illumination light emitted from a light source; an imager configured to capture an image of an observed region illuminated with the illumination light from the light guide; and a fixing member that is made of resin and that has a columnar outer shape, the fixing member being configured to seal around the channel, the light guide, and the imager. The channel is in contact with the imager, and the light guide is in contact with at least one of the channel and the imager, and a contact surface of the channel in contact with the light guide or a contact surface of the imager in contact with the light guide has a groove or a projection formed thereon.

In some embodiments, an endoscope includes the endoscope distal end portion.

In some embodiments, a method of manufacturing an endoscope distal end portion includes: forming a groove or a projection on at least one of a surface of a channel and a surface of the imager; bringing the channel into contact with the imager; supporting the light guide by the groove or the projection to bring the light guide into contact with at least one of the channel and the imager; integrating the channel, the imager, and the light guide together in a state where the channel is in contact with the imager and the light guide is in contact with the at least one of the channel and the imager; placing the integrated channel, imager, and light guide in a mold having a fitting projection that fits in the channel, by fitting the fitting projection into the channel; and forming a fixing member by filling resin into the mold.

In some embodiments, a method of manufacturing an endoscope distal end portion includes: forming a groove or a projection on at least one of a surface of a channel and a surface of the imager; bringing the channel into contact with the imager; supporting the light guide by the groove or the projection to bring the light guide into contact with at least one of the channel and the imager; integrating the channel, the imager, and the light guide together in a state where the channel is in contact with the imager and the light guide is in contact with the at least one of the channel and the imager; placing the integrated channel, imager, and light guide in an outermost casing that has a bottom portion having a hole formed therein and is tubular, the hole being where the channel is fitted in, the bottom portion being made of a transparent material, by fitting the channel into the hole; and forming a fixing member by filling resin into the outermost casing.

The above and other features, advantages and technical and industrial significance of this disclosure will be better understood by reading the following detailed description of presently preferred embodiments of the disclosure, when considered in connection with the accompanying drawings.

DETAILED DESCRIPTION

Described hereinafter as modes for implementation of the disclosure (hereinafter, referred to as "embodiments") are endoscope systems each including an endoscope distal end portion. The disclosure is not limited by these embodiments. Furthermore, each drawing referred to in the following description schematically illustrates shapes, sizes, and positional relations, merely to an extent that allows subject matter of the disclosure to be understood. That is, the disclosure is not limited only to the shapes, sizes, and positional relations, exemplified by the drawings. In addition, a portion that differs in its dimensions and proportions among the drawings may be included also.

First Embodiment

Figure 1:
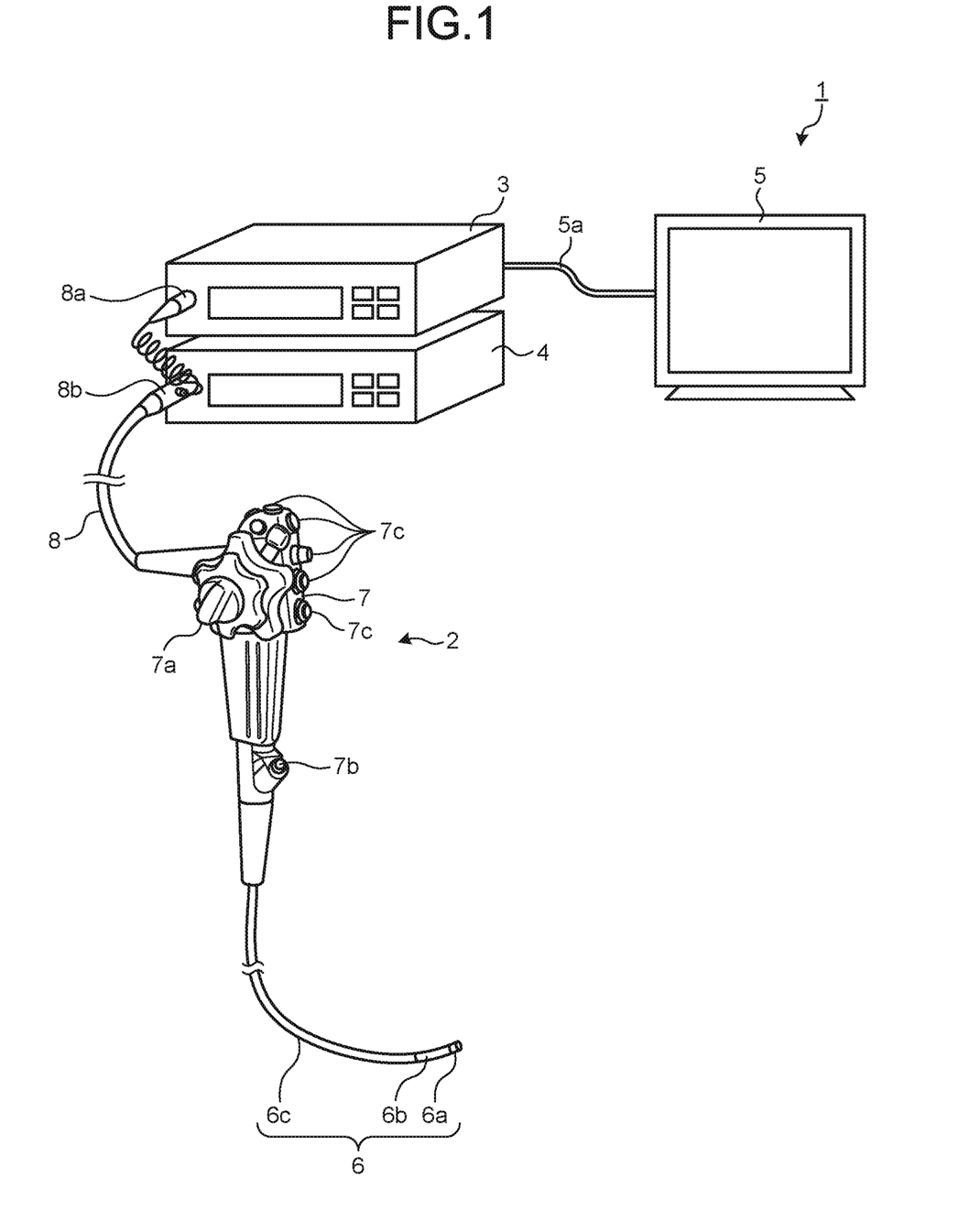
FIG. 1 is a diagram schematically illustrating an overall configuration of an endoscope system according to a first embodiment of the disclosure.

FIG. 1 is a diagram schematically illustrating an overall configuration of an endoscope system 1 according to a first embodiment of the disclosure. As illustrated in FIG. 1, the endoscope system 1 according to the first embodiment includes: an endoscope 2 that is introduced into a subject and generates an in-vivo image signal by capturing an image of the interior of the body of the subject; an information processing device 3 that performs predetermined image processing on the image signal captured by the endoscope 2 and controls each device in the endoscope system 1; a light source device 4 that generates illumination light for the endoscope 2; and a display device 5 that displays an image for the image signal that has been image-processed by the information processing device 3.

The endoscope 2 includes: an insertion unit 6 configured to be inserted into the subject; an operating unit 7 that is on a proximal end side of the insertion unit 6 and is configured to be held by an operator; and a universal cord 8 that extends from the operating unit 7 and is flexible.

The insertion unit 6 is realized by use of a light guide formed of an illumination fiber, an electric cable, or an optical fiber. The insertion unit 6 includes: a distal end portion 6a having a later described built-in imager; a bending portion 6b that is formed of plural bending pieces and is freely bendable; and a flexible tube portion 6c that is provided on a proximal end side of the bending portion 6b and has flexibility. The distal end portion 6a is provided with: an illumination unit that illuminates the interior of the subject via an illumination lens; an observation unit that captures an image of the interior of the subject; an opening section that provides communication with a surgical tool channel; and an air and water feeding nozzle (not illustrated in the drawings).

The operating unit 7 includes: a bending knob 7a that causes the bending portion 6b to bend upward or downward, or leftward or rightward; a surgical tool insertion unit 7b where a surgical tool, such as biological forceps or a laser scalpel, is inserted into a body cavity of the subject; and plural switches 7c for operation of peripheral devices, such as an air feeding device, a water feeding device, and/or a gas feeding device. The surgical tool inserted from the surgical tool insertion unit 7b comes out from the opening section at a distal end of the insertion unit 6 via the surgical tool channel provided inside of the operating unit 7 and the insertion unit 6.

The universal cord 8 is formed by use of: a light guide formed of an illumination fiber; and a cable. The universal cord 8 is branched at a proximal end thereof, and one end portion branching off from the proximal end is a connector 8a and the other proximal end is a connector 8b. The connector 8a is freely attachable to and detachable from a connector of the information processing device 3. The connector 8b is freely attachable to and detachable from the light source device 4. The universal cord 8 transmits the illumination light emitted from the light source device 4, to the distal end portion 6a, via the connector 8b and the light guide formed of the illumination fiber. Furthermore, the universal cord 8 transmits an image signal captured by the later described imager, to the information processing device 3, via the cable and the connector 8a.

The information processing device 3 executes the predetermined image processing on the image signal output from the connector 8a and controls the overall endoscope system 1.

The light source device 4 is formed by use of: a light source that emits light; and a condenser lens. Under control of the information processing device 3, the light source device 4 emits light from the light source and supplies the light as illumination light for the interior of the subject that is a subject to be imaged, to the endoscope 2 connected to the light source device 4 via the connector 8b and the light guide formed of the illumination fiber of the universal cord 8.

The display device 5 is formed by use a display having liquid crystal or organic electroluminescence (EL) used therein. The display device 5 displays, via a video cable 5a, various types of information including the image that has been subjected to the predetermined image processing by the information processing device 3. As a result, the operator is able to perform observation and determination of characteristics, of a desired position in the subject by operating the endoscope 2 while looking at the image (in-vivo image) displayed by the display device 5.

Figure 2:
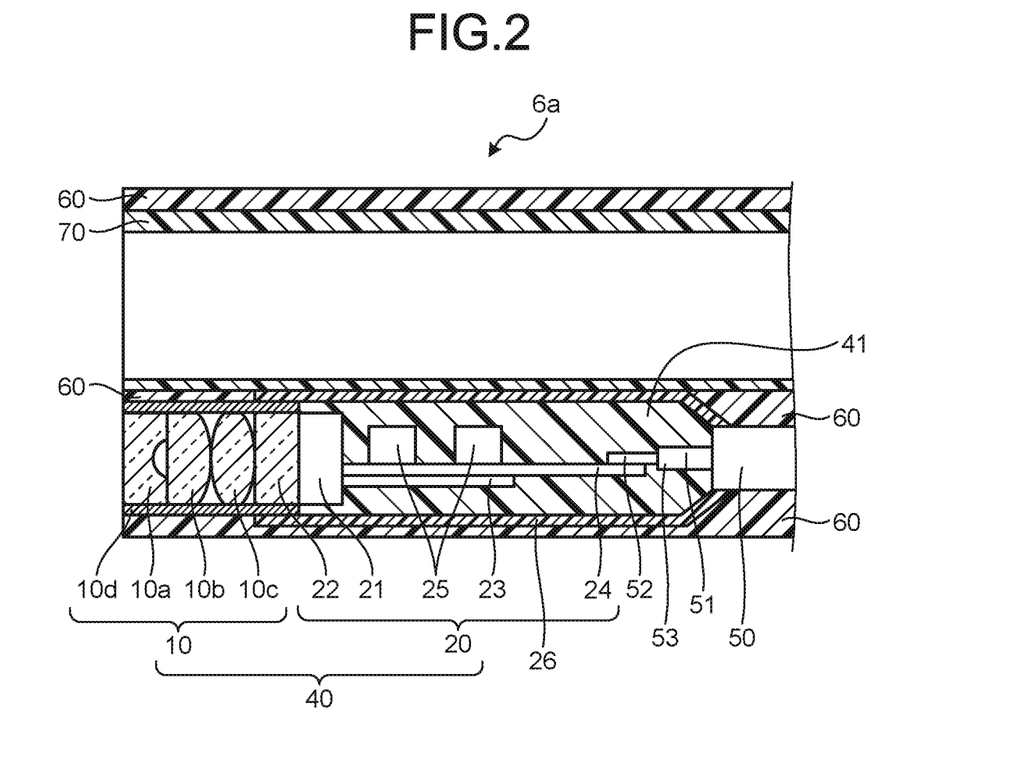
FIG. 2 is a sectional view of a distal end portion of an endoscope, according to the first embodiment of the disclosure, the sectional view being taken on a vertical plane including an optical axis.
Figure 3:
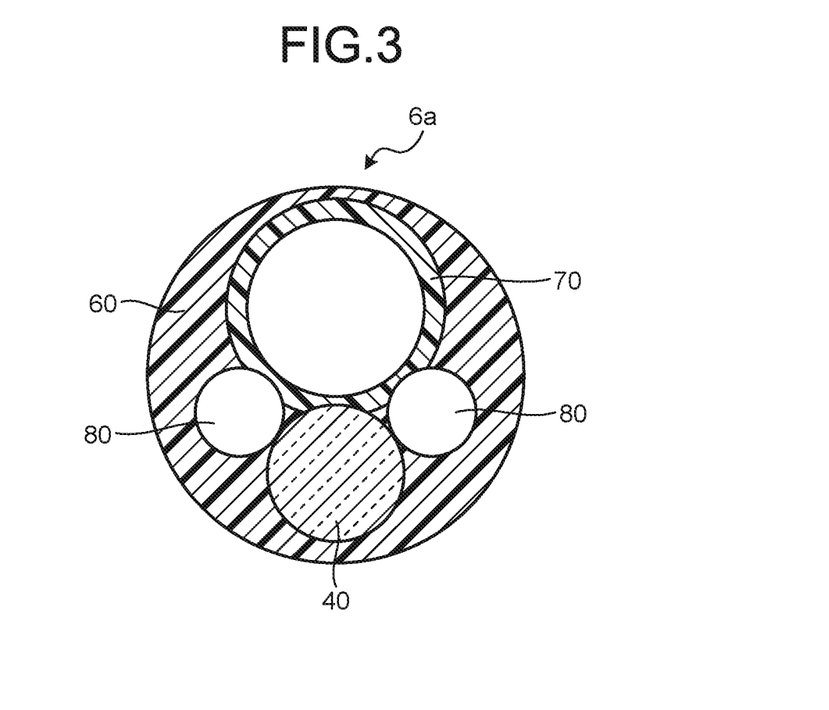
FIG. 3 is a diagram of a cross section of the distal end portion of the endoscope, according to the first embodiment of the disclosure, the cross section being orthogonal to the optical axis.
Figure 4:
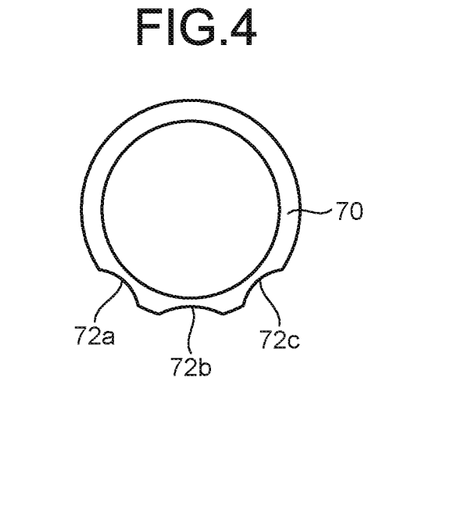
FIG. 4 is a front view of a channel in FIG. 3.

Described next in detail is the distal end portion 6a of the endoscope 2. FIG. 2 is a sectional view of the distal end portion 6a of the endoscope 2 according to the first embodiment of the disclosure, the sectional view being taken on a vertical plane including an optical axis. FIG. 3 is a diagram of a cross section of the distal end portion 6a of the endoscope 2 according to the first embodiment of the disclosure, the cross section being orthogonal to the optical axis. FIG. 4 is a front view of a channel 70 in FIG. 3.

The distal end portion 6a includes: the channel 70 that is where the surgical tool is inserted through and is tubular; light guides 80 that guide the illumination light emitted from the light source device 4; an imager 40 that captures an image of an observed region illuminated with the illumination light from the light guides 80; and a fixing member 60 that seals around the channel 70, the light guides 80, and the imager 40, is made of resin, and has a column shape.

The imager 40 includes a lens unit 10, an imaging unit 20 placed on a proximal end side of the lens unit 10, and a cable assembly 50 having plural signal cables 51 twisted together.

The lens unit 10 includes plural objective lenses 10a, 10b, and 10c, and a lens holder 10d that holds a cover glass 22 described later.

The imaging unit 20 includes: a solid-state imaging element 21, such as a CCD or a CMOS, the solid-state imaging element 21 including a light receiving unit configured to receive light; a cover glass 22 that is bonded to the solid-state imaging element 21 in a state where the cover glass 22 covers the light receiving unit of the solid-state imaging element 21; and a circuit board 24 electrically and mechanically connected to plural contact pins 23 (although only one contact pin 23 is illustrated in FIG. 2) that are provided in a protruding manner on a back surface of the solid-state imaging element 21. The circuit board 24 includes: an electronic component 25 mounted thereon; and core wires 52 of the plural signal cables 51 that supply power to the solid-state imaging element 21, or input or output a signal from or to the solid-state imaging element 21, the core wires 52 being connected closer to a proximal end of the circuit board 24. The imaging unit 20 is held by the lens holder 10d via the cover glass 22 bonded to the solid-state imaging element 21.

A heat-shrinkable tube 26 covers a range from a proximal end portion of the lens holder 10d to a distal end portion of the cable assembly 50. An insulating filler 41 is filled into a space surrounded by the lens holder 10d and the heat-shrinkable tube 26.

The channel 70 is formed of a tube made of polytetrafluoroethylene (PTFE) and having a cross section with a circular inner diameter, and the surgical tool, such as forceps, is inserted into the channel 70. The outer periphery of the channel 70 made of PTFE has preferably been subjected to surface treatment, for improvement in adhesiveness between the channel 70 and the fixing member 60. As illustrated in FIG. 4, grooves 72a, 72b, and 72c have been formed on a contact surface that is the outer periphery of the channel 70 at a distal end portion of the channel 70 and comes into contact with the imager 40 and the light guides 80. The grooves 72a and 72c each have an arc-shape along the outer periphery of the light guides 80, and the groove 72b has a shape along the outer periphery of the imager 40.

The fixing member 60 is made of resin and seals around the channel 70, the light guides 80, and the imager 40 that have been integrated together.

Figure 5:
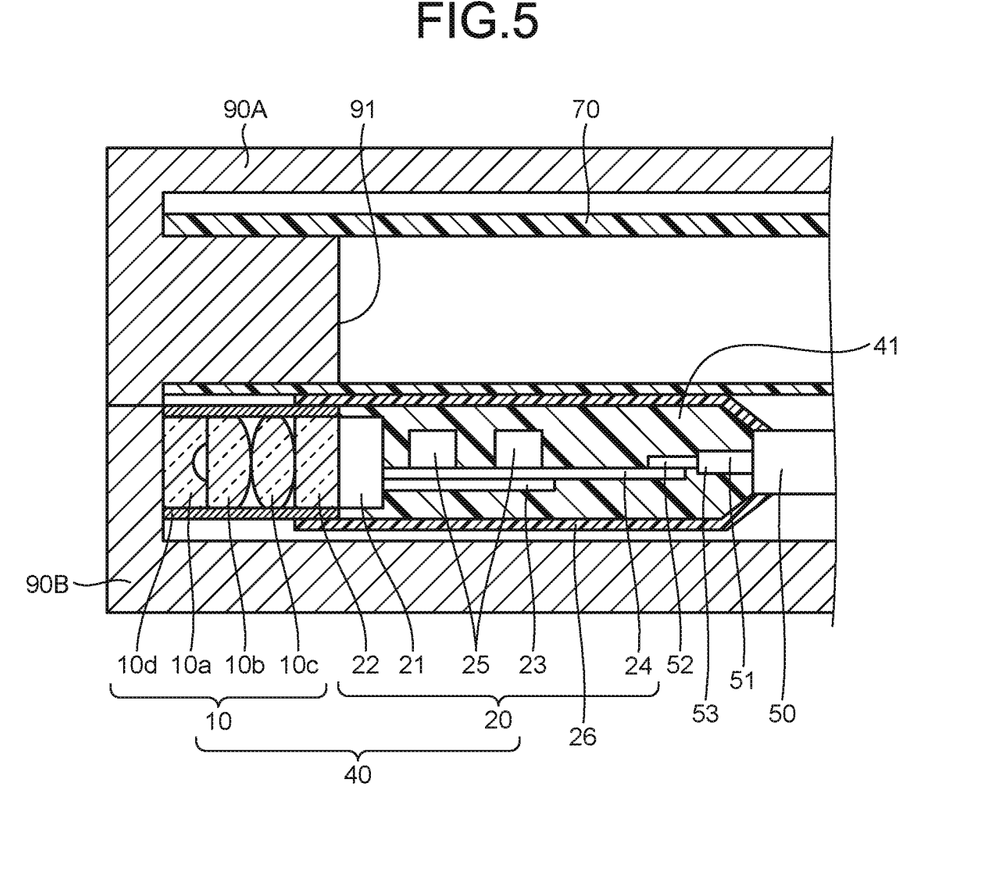
FIG. 5 is a diagram for explanation of a method of manufacturing the distal end portion of the endoscope, according to the first embodiment of the disclosure.

FIG. 5 is a diagram for explanation of a method of manufacturing the distal end portion 6a of the endoscope 2 according to the first embodiment of the disclosure.

For the distal end portion 6a according to the first embodiment to be manufactured, firstly, the channel 70, the light guides 80, and the imager 40 are integrated together in a state where their contact surfaces are in contact with one another. According to the first embodiment, the grooves 72a, 72b, and 72c have been formed on the contact surface of the channel 70, the contact surface coming into contact with the imager 40 and the light guides 80, and the integration is implemented in a state where the imager 40 and the light guide 80 have been fitted in these grooves 72a, 72b, and 72c. This integration may be implemented just by fitting of the imager 40 and the light guides 80 in the grooves 72a, 72b, and 72c of the channel 70 and fixing of a proximal end portion of the channel 70, the imager 40, and the light guides 80 by use of a jig; but for positional accuracy of the imager 40 and the light guides 80, fixing by use of an adhesive is preferable so that the fitted state of the imager 40 and the light guides 80 in the grooves 72a, 72b, and 72c is fixed.

After the channel 70, the imager 40, and the light guides 80 have been integrated together, the fixing member 60 is formed by use of molds 90A and 90B.

As illustrated in FIG. 5, the mold 90A includes a fitting projection 91 that fits in the channel 70; and the integrated channel 70, imager 40, and light guides 80 are placed in the molds 90A and 90B, with the fitting projection 91 fitted in the channel 70.

After the integrated channel 70, imager 40, and light guides 80 have been placed in the molds 90A and 90B, resin is injected into the molds 90A and 90B from an opening of the molds 90A and 90B, the fixing member 60 is molded by curing of the resin, and the distal end portion 6a is thereby manufactured.

By use of the molds 90A and 90B having the fitting projection 91 in molding of the fixing member 60, the channel 70, the imager 40, and the light guides 80 are able to be accurately arranged in the distal end portion 6a.

Furthermore, because the channel 70 having the largest outer diameter and the imager 40 having the second largest outer diameter are integrated together in the state where the imager 40 has been fitted in the groove 72b formed on the contact surface of the channel 70, the distal end portion 6a according to the first embodiment is able to be reduced in diameter. Furthermore, because the fixing member 60 seals around the channel 70, the imager 40, and the light guides 80 that are built-in components, the distal end portion 6a according to the first embodiment is able to be used as-is in the endoscope 2 and the trouble of insertion thereof into a distal end casing is able to be saved. According to the first embodiment, the grooves 72a, 72b, and 72c are formed on the channel 70, but grooves may be formed on the outer periphery of the imager 40.

Figure 6:
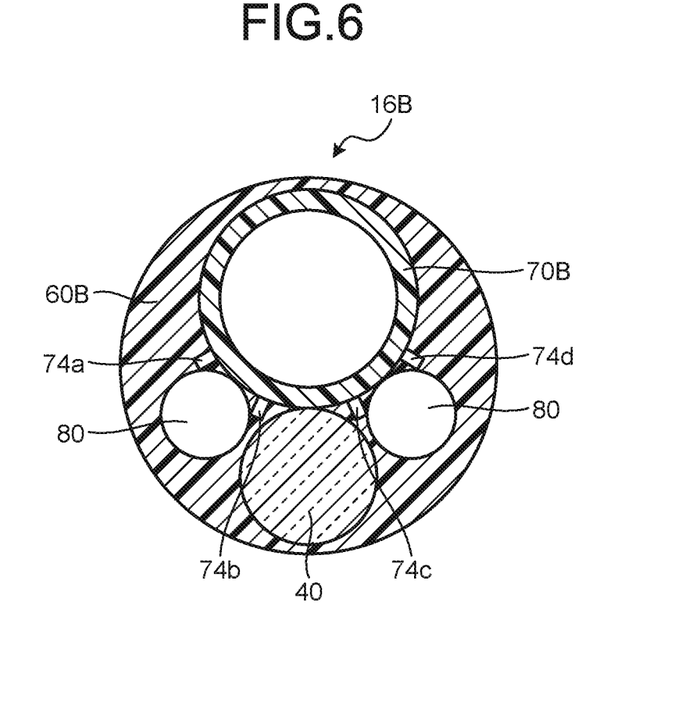
FIG. 6 is a diagram of a cross section of a distal end portion of an endoscope, according to a first modified example of the first embodiment of the disclosure, the cross section being orthogonal to an optical axis.

According to the first embodiment, the distal end portion 6a is reduced in diameter by the formation of the groove 72b on the channel 70 and fitting of the imager 40 in the groove 72b; but the distal end portion 6a is able to be reduced in diameter as long as: the channel 70 and the imager 40 are integrated together in a state where the contact surfaces of the channel 70 and the imager 40 are in contact with each other, and the light guides 80 are integrated with the channel 70 and/or the imager 40 in a state where the contact surfaces of the light guides 80 are in contact with the contact surface of the channel 70 and/or contact surface of the imager 40; and the fixing member 60 seals around the channel 70, the imager 40, and the light guides 80. FIG. 6 is a diagram of a cross section of a distal end portion 16B of an endoscope according to a first modified example of the first embodiment of the disclosure, the cross section being orthogonal to an optical axis.

In the distal end portion 16B of the first modified example, projections 74a, 74b, 74c, and 74d are provided on the outer periphery of a channel 70B, without formation of grooves 72a, 72b, and 72c.

In the distal end portion 16B of the first modified example, one of the light guides 80 is placed between the projection 74a and projection 74b, the other of the light guides 80 is placed between the projection 74c and projection 74d, and the imager 40 is placed between the projection 74b and projection 74c. The light guides 80 and imager 40 are able to be arranged accurately because the light guides 80 and imager 40 are arranged between the projections 74a, 74b, 74c, and 74d formed at predetermined positions on the outer periphery of the channel 70B.

Furthermore, because the channel 70B is integrated with the imager 40 in a state where the channel 70B is in contact with the imager 40, and the channel 70B is integrated with the light guides 80 in a state where the channel 70B is in contact with the light guides 80, and the integrated channel 70B and imager 40 and the integrated channel 70B and light guides 80 are fixed by sealing with a fixing member 60B; a distal end casing does not need to be used and the distal end portion 16B is able to be reduced in diameter.

Figure 7:
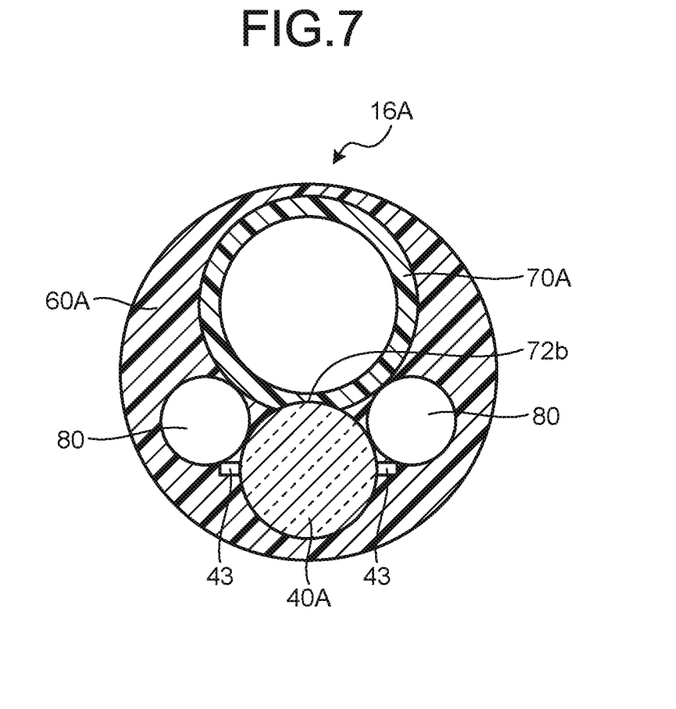
FIG. 7 is a diagram of a cross section of a distal end portion of an endoscope, according to a second modified example of the first embodiment of the disclosure, the cross section being orthogonal to an optical axis.

Furthermore, as long as a distal end portion is able to be reduced in diameter and positional accuracy of its built-in components is able to be improved, both groove/grooves and projection/projections may be used. FIG. 7 is a diagram of a cross section of a distal end portion 16A of an endoscope according to a second modified example of the first embodiment of the disclosure, the cross section being orthogonal to an optical axis.

In the distal end portion 16A of the second modified example, a groove 72b where an imager 40A is fitted in has been formed on the outer periphery of a channel 70A. Furthermore, projections 43 that define positions where the light guides 80 are to be placed have been formed on the outer periphery of the imager 40A.

In the distal end portion 16A of the second modified example, the light guides 80 are placed between the projections 43 formed at predetermined positions and the channel 70A, and the imager 40A is placed by being fitted in the groove 72b of the channel 70A. Because the imager 40A is positioned by the groove 72b formed on the outer periphery of the channel 70A and the light guides 80 are placed between the outer periphery of the channel 70A and the projections 43 on the imager 40A, the imager 40A and the light guides 80 are able to be arranged accurately.

Furthermore, because the channel 70A and the imager 40A are integrated together in a state where the channel 70A is in contact with the imager 40A, and the light guides 80 are integrated with the channel 70A and imager 40A in a state where the light guides 80 are in contact with the channel 70A and imager 40A, and the integrated channel 70A, imager 40A, and light guides 80 are fixed by sealing with a fixing member 60A; a distal end casing does not need to be used and the distal end portion 16A is able to be reduced in diameter.

Figure 8:
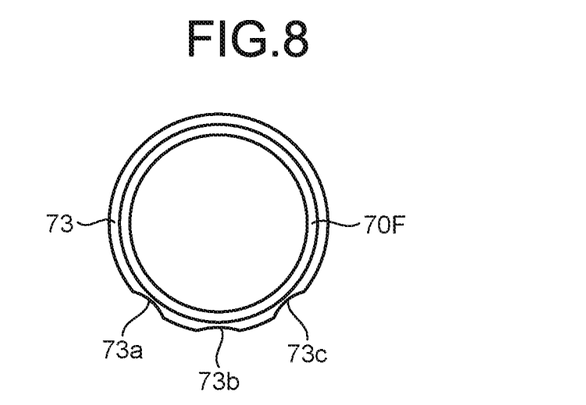
FIG. 8 is a front view of a channel according to a third modified example of the first embodiment of the disclosure.

Furthermore, although the groove 72a and the like are formed by direct processing of the channel 70, according to the first embodiment; a covering that covers the outer periphery of the channel 70 may be provided and grooves may be formed on the covering. FIG. 8 is a front view of a channel 70F according to a third modified example of the first embodiment of the disclosure. The channel 70F according to the third modified example includes a covering 73 that covers the outer periphery of the channel 70F, the covering 73 being made of resin.

Grooves 73a, 73b, and 73c have been formed on a contact surface of the covering 73, the contact surface coming into contact with an imager and light guides, and integration is implemented with the imager and the light guides being fitted in these grooves 73a, 73b, and 73c. The imager and the light guides are fitted in the grooves 73a, 73b, and 73c of the covering 73 covering the channel 70F and are fixed by sealing with a fixing member, and a distal end casing thus does not need to be used and a distal end portion is thus able to be reduced in diameter. Furthermore, because the imager and the light guides are positioned by the grooves 73a, 73b, and 73c, the imager and the light guides are able to be arranged accurately.

Although the grooves 73a, 73b, and 73c have been formed on the channel 70F according to the third modified example, projections for positioning of light guides may be provided, instead of the grooves 73a and 73c, on the covering 73 or on the imager.

Furthermore, reduction in the diameter of the distal end portion and improvement in the positional accuracy of its built-in components may be achieved by, instead of the formation of the covering 73 on the channel 70F, formation of a covering on the imager and formation of grooves on a surface of the covering that covers the imager, the surface coming into contact with a channel and the light guides.

Second Embodiment

Figure 9:
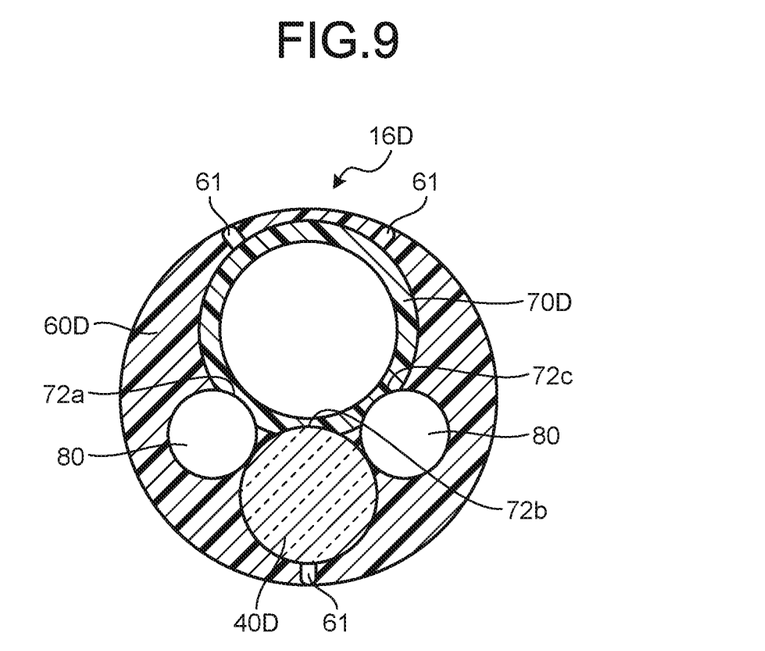
FIG. 9 is a diagram of a cross section of a distal end portion of an endoscope, according to a second embodiment of the disclosure, the cross section being orthogonal to an optical axis.

FIG. 9 is a diagram of a cross section of a distal end portion 16D of an endoscope according to a second embodiment of the disclosure, the cross section being orthogonal to an optical axis. In the distal end portion 16D according to the second embodiment, positioning projections 61 made of resin and each having a distal end that is exposed at the outer periphery of a fixing member 60D have been formed on the outer periphery of a channel 70D and on the outer periphery of an imager 40D.

Figure 10:
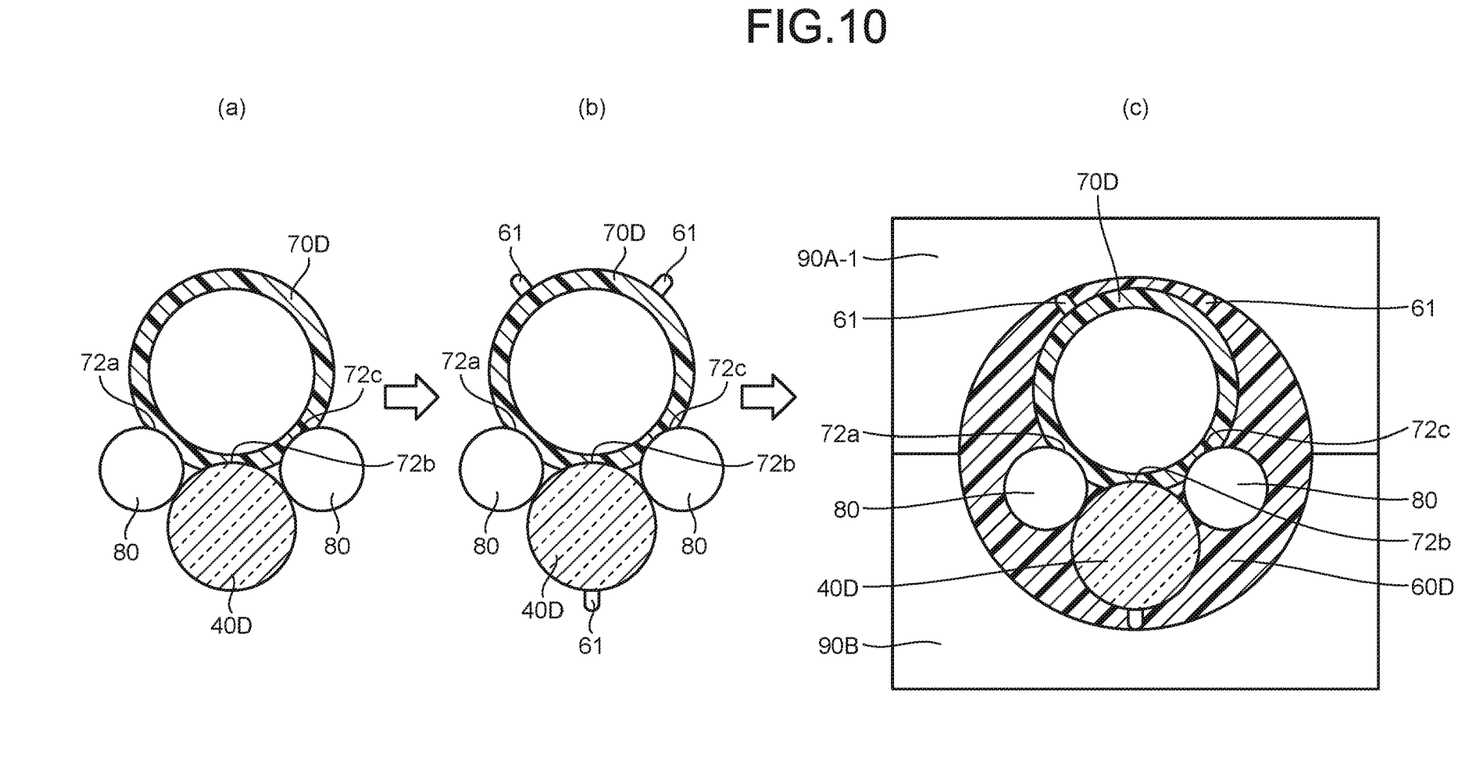
FIG. 10 is a diagram for explanation of a method of manufacturing the distal end portion of the endoscope according to the second embodiment of the disclosure.

FIG. 10 is a diagram for explanation of a method of manufacturing the distal end portion 16D according to the second embodiment of the disclosure. As illustrated in (a) of FIG. 10, the imager 40D and the light guides 80 are fitted in grooves 72a, 72b, and 72c formed on a contact surface of the channel 70D, and the channel 70D, the imager 40D, and the light guides 80 are integrated together. This step is the same as that of the first embodiment.

Thereafter, the positioning projections 61 made of resin are formed at at least three positions on the outer periphery of the integrated channel 70D, imager 40D and light guides 80, for example, at a total of three positions according to the second embodiment, as illustrated in (b) of FIG. 10, the three positions including two positions on the outer periphery of the channel 70D and one position on the outer periphery of the imager 40D. The positioning projections 61 each have a size allowing the positioning projections 61 to contact the inner periphery of molds 90A-1 and 90B for molding of the fixing member 60D, as illustrated in (c) of FIG. 10, when the integrated channel 70D, imager 40D, and light guides 80 are placed in the molds 90A-1 and 90B.

After the integrated channel 70D, imager 40D, and light guides 80 have been placed in the molds 90A-1 and 90B, resin is injected into the molds 90A-1 and 90B from an opening of the molds 90A-1 and 90B, the fixing member 60D is molded by curing of the resin, and the distal end portion 16D is thereby manufactured. By the positioning projections 61 having the size allowing the positioning projections 61 to contact the inner periphery of the molds 90A-1 and 90B, the distal ends of the positioning projections 61 are exposed at the outer periphery of the fixing member 60D.

Because the distal end portion 16D according to the second embodiment includes the positioning projections 61, even if the molds 90A-1 and 90B without a fitting projection 91 are used, the distal end portion 16D excellent in positional accuracy of its built-in components is able to be manufactured.

Furthermore, in the distal end portion 16D according to the second embodiment, because the grooves 72a, 72b, and 72c are formed on the contact surface of the channel 70D, the contact surface coming into contact with the imager 40D and the light guides 80, and fixing is performed by sealing with the fixing member 60D after the imager 40D and the light guides 80 have been fitted in these grooves 72a, 72b, and 72c, a distal end casing does not need to be used and the distal end portion 16D is able to be reduced in diameter.

Third Embodiment

Figure 11:
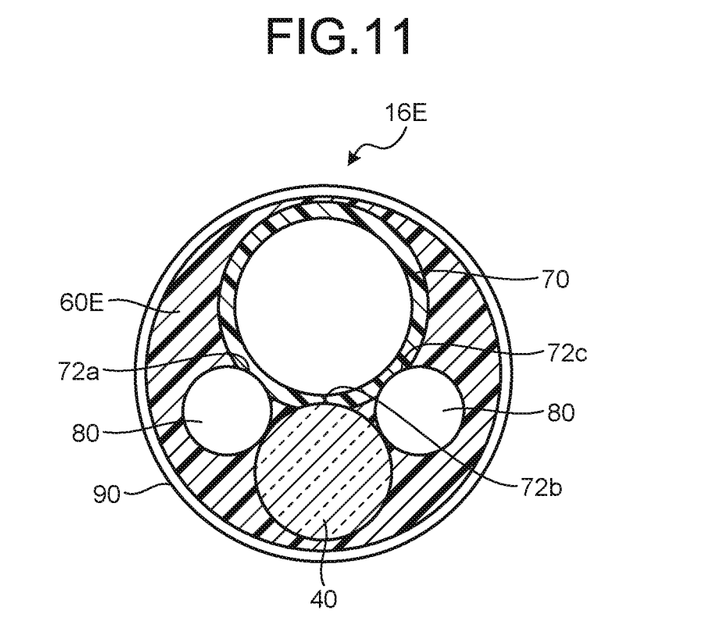
FIG. 11 is a diagram of a cross section of a distal end portion according to a third embodiment of the disclosure, the cross section being orthogonal to an optical axis.

FIG. 11 is a diagram of a cross section of a distal end portion 16E of an endoscope according to a third embodiment of the disclosure, the cross section being orthogonal to an optical axis. The distal end portion 16E according to the third embodiment includes an outermost casing 90 that accommodates therein a channel 70, an imager 40, and light guides 80, and includes a bottom portion 92 having, formed therein, a hole 93 where the channel 70 is fitted in, the outermost casing 90 being tubular, the bottom portion 92 being made of a transparent material.

Figure 12:
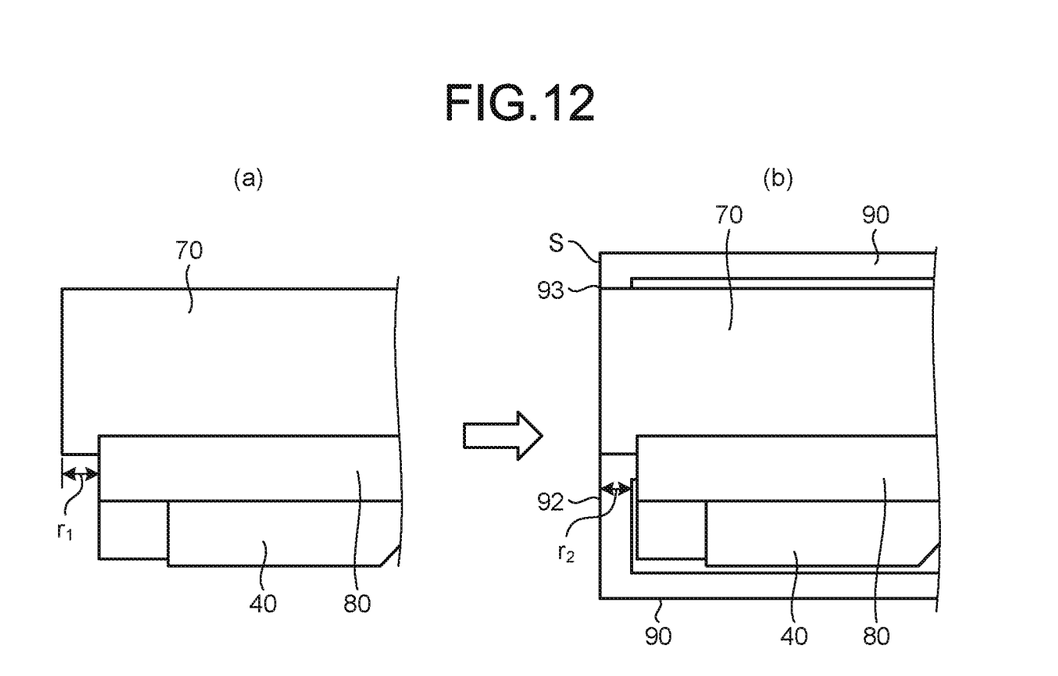
FIG. 12 is a diagram for explanation of a method of manufacturing the distal end portion according to the third embodiment of the disclosure.

FIG. 12 is a diagram for explanation of a method of manufacturing the distal end portion 16E according to the third embodiment of the disclosure. According to the first and second embodiments, a distal end face of the integrated channel 70, imager 40, and light guides 80 is flat, but according to the third embodiment, as illustrated in (a) of FIG. 12, a distal end of the channel 70 protrudes from a distal end of the imager and the light guides 80 by r1.

The channel 70, imager 40, and the light guides 80 that have been integrated together, with the distal end of the channel 70 protruding from the distal end of the imager 40 and the light guides 80, are placed inside the outermost casing 90 that functions also as a mold, as illustrated in (b) of FIG. 12. In this placement, the channel 70 is fitted in the hole 93 having a diameter that is slightly larger than an outer diameter of the channel 70, and the distal end of the channel 70 is positioned in line with a distal end S of the bottom portion 92. For the distal end of the channel 70 and the distal end S of the bottom portion 92 to be on the same plane, the amount of protrusion r1 of the channel 70 is preferably substantially the same as a thickness r2 of the bottom portion 92.

After the integrated channel 70, imager 40, and light guides 80 have been placed in the outermost casing 90, resin is injected into the mold from an opening of the outermost casing 90, a fixing member 60E is molded by curing of the resin, and the distal end portion 16E is thereby manufactured. According to the third embodiment, because the outermost casing 90 is used also as the mold, the fixing member 60E is able to be reduced in thickness and the distal end portion 16E is able to be reduced in diameter. Furthermore, because the channel 70 is fitted into the hole 93, positional accuracy of built-in components in the outermost casing 90 is able to be improved.

According to the disclosure, distal end portions of endoscopes are able to be reduced in diameter and positional accuracy of built-in components accommodated in the distal end portions is able to be improved.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope distal end portion, comprising:
   a channel that is tubular, the channel being where a surgical tool is to be inserted in;
   a light guide configured to guide illumination light emitted from a light source;
   an imager configured to capture an image of an observed region illuminated with the illumination light from the light guide, the imager comprises one or more lenses and an imaging sensor; and
   a fixing member that is made of resin and that has a columnar outer shape, the fixing member being configured to seal around the channel, the light guide, and the imager, and
   a covering that is made of resin, the covering being configured to cover an outer periphery of the channel or an outer periphery of the imager, wherein
   a contact surface of the covering on the channel in contact with the imager or a contact surface of the covering on the imager in contact with the channel has a groove formed thereon, and
   a contact surface of the covering on the channel in contact with the light guide or a contact surface of the covering on the imager in contact with the light guide has a groove or a projection formed thereon.

2. The endoscope distal end portion according to claim 1, wherein at least three positioning projections made of resin, each having a distal end exposed at an outer periphery of the fixing member, are formed on one of the outer periphery of the channel and an outer periphery of the covering on the channel and on one of the outer periphery of the imager and an outer periphery of the covering on the imager.

3. The endoscope distal end portion according to claim 1, further comprising:
   an outermost casing that has a bottom portion having a hole formed therein and is tubular, the hole being where the channel is fitted in, the bottom portion being made of a transparent material, the outermost casing being configured to accommodate therein the channel, the imager, and the light guide that have been integrated together, wherein
   the fixing member is formed by resin being filled in between: the outermost casing; and the integrated channel, imager, and light guide.

4. An endoscope, comprising:
   the endoscope distal end portion according to claim 1.

5. A method of manufacturing the endo scope distal end portion according to claim 1, including:
   forming a groove or a projection on at least one of a surface of a channel and a surface of the imager;
   bringing the channel into contact with the imager;
   supporting the light guide by the groove or the projection to bring the light guide into contact with at least one of the channel and the imager;
   integrating the channel, the imager, and the light guide together in a state where the channel is in contact with the imager and the light guide is in contact with the at least one of the channel and the imager;
   placing the integrated channel, imager, and light guide in a mold having a fitting projection that fits in the channel, by fitting the fitting projection into the channel; and
   forming a fixing member by filling resin into the mold.

6. A method of manufacturing the endo scope distal end portion according to claim 3, including:
   forming a groove or a projection on at least one of a surface of a channel and a surface of the imager;
   bringing the channel into contact with the imager;
   supporting the light guide by the groove or the projection to bring the light guide into contact with at least one of the channel and the imager;
   integrating the channel, the imager, and the light guide together in a state where the channel is in contact with the imager and the light guide is in contact with the at least one of the channel and the imager;
   placing the integrated channel, imager, and light guide in an outermost casing that has a bottom portion having a hole formed therein and is tubular, the hole being where the channel is fitted in, the bottom portion being made of a transparent material, by fitting the channel into the hole; and
   forming a fixing member by filling resin into the outermost casing.

* * * * *